United States Patent
Briscoe

(10) Patent No.: US 11,103,352 B2
(45) Date of Patent: Aug. 31, 2021

(54) ORTHOPAEDIC POLYMER-ON-POLYMER BEARINGS

(71) Applicant: Invibio Limited, Thornton Cleveleys (GB)

(72) Inventor: Adam Briscoe, Thornton Cleveleys (GB)

(73) Assignee: INVIBIO LIMITED, Lancashire (GB)

( * ) Notice: Subject to any disclaimer, the term of this patent is extended or adjusted under 35 U.S.C. 154(b) by 57 days.

(21) Appl. No.: 16/538,130

(22) Filed: Aug. 12, 2019

(65) Prior Publication Data

US 2019/0358040 A1 Nov. 28, 2019

Related U.S. Application Data

(63) Continuation of application No. 14/438,672, filed as application No. PCT/GB2013/052770 on Oct. 24, 2013, now abandoned.

(30) Foreign Application Priority Data

Nov. 1, 2012 (GB) ...................................... 1219686

(51) Int. Cl.
  *A61F 2/30* (2006.01)
  *A61L 27/44* (2006.01)
  *A61L 27/16* (2006.01)

(52) U.S. Cl.
  CPC ............ *A61F 2/30* (2013.01); *A61F 2/30942* (2013.01); *A61L 27/16* (2013.01); *A61L 27/446* (2013.01); *A61F 2002/30957* (2013.01); *A61F 2210/0076* (2013.01); *A61L 2430/24* (2013.01)

(58) Field of Classification Search
  CPC ............... A61F 2/30; A61F 2/38; A61L 27/16
  See application file for complete search history.

(56) References Cited

U.S. PATENT DOCUMENTS

| | | | |
|---|---|---|---|
| 6,228,900 | B1 | 5/2001 | Shen et al. |
| 2007/0270691 | A1 | 11/2007 | Bailey et al. |
| 2009/0276051 | A1 | 11/2009 | Arramon et al. |
| 2010/0312348 | A1 | 12/2010 | Wang et al. |
| 2012/0101185 | A1 | 4/2012 | Valentine et al. |

FOREIGN PATENT DOCUMENTS

| | | |
|---|---|---|
| EP | 1857073 A1 | 11/2007 |
| GB | 2435648 A | 9/2007 |
| WO | 2007016795 A1 | 2/2007 |

OTHER PUBLICATIONS

International Search Report and Written Opinion of corresponding International Application No. PCT/GB2013/052770; 11 pages; dated Aug. 1, 2014.
Search Report of corresponding UK Patent Application No. GB1318797.6; dated May 15, 2014; 1 page.

*Primary Examiner* — Brian A Dukert
(74) *Attorney, Agent, or Firm* — Shumaker, Loop & Kendrick, LLP

(57) ABSTRACT

The invention is a prosthetic joint, for example, knee joint, including a first joint component which is preferably polyetheretherketone containing barium sulphate and a second joint component which is preferably a polyolefin.

11 Claims, 1 Drawing Sheet

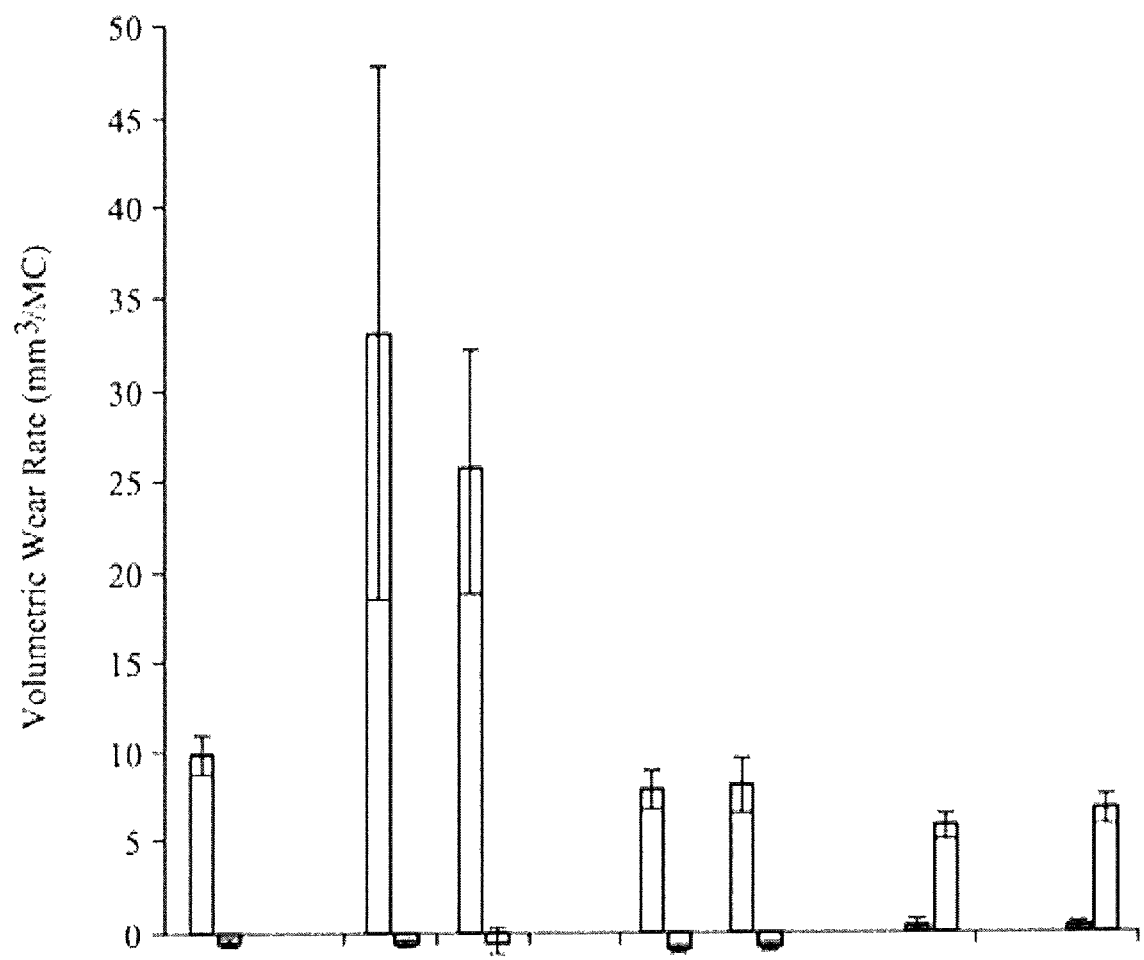

ORTHOPAEDIC POLYMER-ON-POLYMER BEARINGS

CROSS REFERENCE TO RELATED APPLICATIONS

This application is a continuation claiming the benefit and priority to U.S. National Stage patent application Ser. No. 14/438,672 filed on Apr. 27, 2015, which claims priority to International Application No. PCT/GB2013/052770 filed on Oct. 24, 2013, which claims priority to UK Patent Application No. 1219686.1 filed on Nov. 1, 2012, all of which are hereby incorporated by reference in their entireties.

TECHNICAL FIELD AND BACKGROUND OF THE INVENTION

This invention refers to orthopaedic polymer-on-polymer bearings and particularly, although not exclusively, relates to bearings comprising a hard part, for example a polyaryletherketone part bearing on a softer part, for example a polyethylene part.

U.S. Patent Application Publication No. 2010/0312348 A1 (Howmedica Osteonics Corp.) describes an orthopaedic prosthesis joint comprising a joint couple having a first bearing surface made of a polyaryletherketone (PAEK) and a second joint component having a second bearing surface made of a material which is softer than the PAEK, the first and second bearing surfaces being in sliding engagement with one another. Polyethylene is exemplified as the preferred second bearing surface.

The PAEK, or more specifically the polyetheretherketone (PEEK) exemplified, is unfilled and in the example PEEK heads made are polished, presumably to reduce their roughness with the aim of reducing abrasion when the PEEK slides over the polyethylene thereby to reduce wear on the polyethylene.

However, a problem exists with the prosthetic joint in that it is difficult to visualise the joint under X-rays and, accordingly, it is difficult to fully assess the joint when implanted in the human body. Prior to the present invention, it was thought to be undesirable to include fillers in the harder PAEK part. Such fillers would increase roughness (Ra) of the harder part and/or protrude from the surface. If the filler was significantly harder than the PAEK part or the material of the counterface of the second joint component, there would be a risk of severe abrasion and/or wear on the softer counterface in use. For example, observations on a hard part comprising PEEK containing carbon fibre, bearing against a softer polyethylene counterface, show the detrimental effect of adding the carbon fibre filler—wear on the polyethylene part increases significantly. This is described in the examples which follow. Thus, prior to the present invention, the problem of improving visualisation of a joint of the type described under X-rays had not been solved.

SUMMARY OF THE INVENTION

It is an object of the present invention to improve visualisation of a prosthetic joint under X-rays.

It is an object of the present invention to solve the stated problem without a significant detrimental effect on wear.

According to a first aspect of the invention, there is provided an orthopaedic prosthetic joint having a joint couple. The joint couple may include a first joint component having a first bearing surface comprising a first material which comprises a first polymer; and a second joint component having a second bearing surface comprising a second material which comprises a second polymer.

According to such an aspect of the invention: the first and second bearing surfaces are in sliding engagement with one another; the first polymer is harder than said second polymer; wherein said first material includes barium sulphate. Unless otherwise stated herein, the relative hardness of the material of said first and second bearing surfaces may be assessed by the Ball indentation method described in ISO 2039-1:2001.

A hardness ratio may be defined as the hardness of the first material divided by the hardness of the second material. The hardness ratio may be at least 2, 3, 4, 5 or 6. It may be less than 10, 9 or 8. It is suitably in the range 4 to 9.

Said first material may be a polyacetal, for example DELRIN (Trade Mark) polyacetal or it may be a polyaryletherketone (PAEK). Said second material may be a polyolefin, for example polyethylene, a polyurethane or a polyamide.

According to a second aspect of the invention, there is provided an orthopaedic prosthetic joint comprising a joint couple having a joint couple. The joint couple may include a first joint component having a first bearing surface made of a first polymer; and a second joint component having a second bearing surface made of a second polymer. According to such an aspect of the invention: the first and second bearing surfaces are in sliding engagement with one another; the first bearing surface is made of a first material which is harder than a second material from which the second joint surface is made; and the first material comprise a polyaryletherketone and barium sulphate.

The orthopaedic prosthetic joint of the first and/or second aspects may be as described further below.

Said barium sulphate may have a $D_{10}$ particle size in the range 0.1 to 1.0 µm; a $D_{50}$ particle size suitably in the range 0.5 µm to 2 µm and a $D_{90}$ particle size suitably in the range 1.0 µm to 5 µm. The $D_{10}$ may be in the range 0.1 to 0.6 µm, preferably 0.2 to 0.5 µm. The $D_{50}$ may be in the range 0.7 µm to 1.5 µm, preferably 0.8 to 1.3 µm. The $D_{90}$ may be in the range 1.5 to 3 µm, preferably in the range 2.0 to 2.5 µm.

Unless otherwise stated, particle sizes may be assessed by laser diffraction, suitably in accordance with ISO13320.

The ratio of the wt % of barium sulphate to the wt % of said first polymer may be greater than 0.04, is suitably greater than 0.07, is preferably greater than 0.10, is more preferably greater than 0.13, and is especially greater than 0.16. In some cases, said ratio may be greater than 0.20 or 0.22. The ratio may be less than 0.4, or less than 0.3.

Said barium sulphate is preferably intimately mixed with the first polymer, suitably so the barium sulphate and first polymer define a substantially homogenous mixture. Said first material preferably comprises a said homogenous mixture.

Said first bearing surface (for example said first material) may include at least 1 wt %, suitably at least 2 wt %, preferably at least 3 wt % barium sulphate. The amount of barium sulphate may be 30 wt % or less, 20 wt % or less, for example 15 wt % or less. Said first bearing surface (for example said first material) may include 2 to 10 wt %, for example 3 to 8 wt % barium sulphate.

The ratio comprising the wt % of said first polymer divided by the wt % of said barium sulphate in said bearing surface (for example in said first material) is suitably in the range 5 to 25, preferably in the range 9 to 18.

Said first material preferably includes less than 5 wt % of fibres, for example less than 2 wt % or less than 0.5 wt %. It preferably includes no fibres.

A preferred polyaryletherketone has a repeat unit of formula (I)

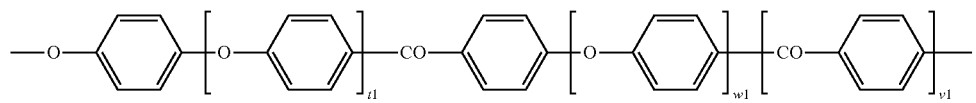

where t1 and w1 independently represent 0 or 1 and v1 represents 0, 1 or 2.

Said polyaryletherketone suitably includes at least 90, 95 or 99 mol % of repeat unit of formula I.

Said polyaryletherketone preferably consists essentially of a repeat unit of formula I. Preferred polymeric materials comprise (especially consist essentially of) a said repeat unit wherein t1=1, v1=0 and w1=0; t1=0, v1=0 and w1=0; t1=0, w1=1, v1=2; or t1=0, v1=1 and w1=0. More preferred comprise (especially consist essentially of) a said repeat unit wherein t1=1, v1=0 and w1=0; or t1=0, v1=0 and w1=0. The most preferred comprises (especially consists essentially of) a said repeat unit wherein t1=1, v1=0 and w1=0.

In preferred embodiments, said polymeric material is selected from polyetheretherketone, polyetherketone, polyetherketoneetherketoneketone and polyetherketoneketone. In a more preferred embodiment, said polymeric material is selected from polyetherketone and polyetheretherketone. In an especially preferred embodiment, said polymeric material is polyetheretherketone.

Said polyaryletherketone may have a Notched Izod Impact Strength (specimen 80 mm×10 mm×4 mm with a cut 0.25 mm notch (Type A), tested at 23° C., in accordance with ISO180) of at least 4 KJm$^{-2}$, preferably at least 5 KJm$^{-2}$, more preferably at least 6 KJm$^{-2}$. Said Notched Izod Impact Strength, measured as aforesaid, may be less than 10 KJm$^{-2}$, suitably less than 8 KJm$^{-2}$. The Notched Izod Impact Strength, measured as aforesaid, may be at least 3 KJm$^{-2}$, suitably at least 4 KJm$^{-2}$, preferably at least 5 KJm$^{-2}$. Said impact strength may be less than 50 KJm$^{-2}$, suitably less than 30 KJm$^{-2}$.

Said polyaryletherketone suitably has a melt viscosity (MV) of at least 0.06 kNsm$^{-2}$, preferably has a MV of at least 0.09 kNsm$^{-2}$, more preferably at least 0.12 kNsm$^{-2}$, especially at least 0.15 kNsm$^{-2}$. Advantageously, the MV may be at least 0.35 kNsm$^{-2}$ and especially at least 0.40 kNsm$^{-2}$ An MV of 0.45 kNsm$^{-2}$ has been found to be particularly advantageous in the manufacture of accurate, strong frameworks.

MV is suitably measured using capillary rheometry operating at 400° C. at a shear rate of 1000s$^{-1}$ using a tungsten carbide die, 0.5 mm×3.175 mm.

Said polyaryletherketone may have a MV of less than 1.00 kNsm$^{-2}$, preferably less than 0.5 kNsm$^{-2}$.

Said polyaryletherketone may have a MV in the range 0.09 to 0.5 kNsm$^{-2}$, preferably in the range 0.14 to 0.5 kNsm$^{-2}$, more preferably in the range 0.4 to 0.5 kNsm$^{-2}$.

Said polyaryletherketone may have a tensile strength, measured in accordance with ISO527 (specimen type 1b) tested at 23° C. at a rate of 50 mm/minute of at least 20 MPa, preferably at least 60 MPa, more preferably at least 80 MPa. The tensile strength is preferably in the range 80-110 MPa, more preferably in the range 80-100 MPa.

Said polyaryletherketone may have a flexural strength, measured in accordance with ISO178 (80 mm×10 mm×4 mm specimen, tested in three-point-bend at 23° C. at a rate of 2 mm/minute) of at least 50 MPa, preferably at least 100 MPa, more preferably at least 145 MPa. The flexural strength is preferably in the range 145-180 MPa, more preferably in the range 145-164 MPa.

Said polyaryletherketone may have a flexural modulus, measured in accordance with ISO178 (80 mm×10 mm×4 mm specimen, tested in three-point-bend at 23° C. at a rate of 2 mm/minute) of at least 1 GPa, suitably at least 2 GPa, preferably at least 3 GPa, more preferably at least 3.5 GPa. The flexural modulus is preferably in the range 3.5-4.5 GPa, more preferably in the range 3.5-4.1 GPa.

Said polyaryletherketone may be amorphous or semi-crystalline. It is preferably crystallisable. It is preferably semi-crystalline.

The level and extent of crystallinity in a polymer is preferably measured by wide angle X-ray diffraction (also referred to as Wide Angle X-ray Scattering or WAXS), for example as described by Blundell and Osborn (Polymer 24, 953, 1983). Alternatively, crystallinity may be assessed by Differential Scanning calorimetry (DSC).

The level of crystallinity of said polyaryletherketone may be at least 1%, suitably at least 3%, preferably at least 5% and more preferably at least 10%. In especially preferred embodiments, the crystallinity may be greater than 25%. It may be less than 50% or less than 40%.

The main peak of the melting endotherm (Tm) of said polyaryletherketone (if crystalline) may be at least 300° C.

Said second material may be selected from a polyethylene, a polyurethane, a polyamide and a composite of these polymers. It preferably comprises polyethylene.

Said second material preferably comprises at least 60 wt %, more preferably at least 75 wt %, especially at least 90 wt % of the polymeric material selected from polyethylene, a polyurethane and polyamide. Said second material preferably includes a single type of polymeric material.

Said second material preferably includes at least 90 wt %, more preferably at least 96 wt %, especially at least 99 wt % of polyethylene. The balance may comprise additives and/or fillers, for example an anti-oxidant such as Vitamin C.

Said polyethylene may be crosslinked. It is preferably crosslinked, for example by irradiation. It may comprise UHMWPE. Preferably, it comprises UHMWPE which has been crosslinked at least three times by irradiation. It may comprise X3™ UHMWPE of Stryker Corporation, crosslinked as described in U.S. Pat. No. 7,517,919.

Said first bearing surface may be defined by a coating of said first polymer on another body for example a solid body. Preferably, however, said first bearing surface does not comprise a coating. Preferably, said first joint component comprises a self-supporting body made from said first polymer wherein said body incorporates said first bearing surface, suitable as an integral part thereof. Preferably, at least 80 wt % of said first joint component is made up of said first polymer; the balance may be said barium sulphate. Preferably, the sum of the wt % of said first polymer (especially polyetheretherketone) and barium sulphate in said first joint component is at least 90 wt %, preferably at least 95 wt %, more preferably at least 99 wt %. Preferably, said first joint component consists essentially of polyetheretherketone and barium sulphate.

Said first joint component may include at least 0.5 g, preferably at least 1 g, more preferably at least 5 g of said first polymer. Said first joint component may include less than 1 kg of said first polymer.

Said first joint component may have a weight of at least 1 g, preferably at least 5 g. The weight may be less than 1 kg.

Said second bearing surface may be defined by a coating of said second polymer on another body for example a solid body. Preferably, however, said second bearing surface does not comprise a coating. Preferably, said second joint component comprises a self-supporting body made from said second polymer wherein said body incorporates said second bearing surface, suitably as an integral part thereof. Suitably, at least 80 wt % preferably at least 90 wt %, more preferably at least 95 wt %, especially at least 99 wt % of said second joint component is made up of said second polymer.

Said second joint component may include at least 0.5 g, preferably at least 1 g, more preferably at least 5 g of said second polymer. Said second joint component may include less than 1 kg of said second polymer. Said second joint component may include less than 1 kg of said second polymer. Said bearing surface of said second joint component may include 0.5 g, preferably at least 1 g, more preferably at least 5 g of said second polymer.

Said second joint component may have a weight of at least 1 g, preferably at least 5 g. The weight may be less than 1 kg.

In the prosthetic joint, said first and second joint components may be movable relative to one another. For example, a bearing surface of one of the components may be arranged to slide over a bearing surface of the other component. Said first and second bearing components may be pivotable relative to one another.

Preferably the entire area of the first bearing surface which area contacts the second bearing surface comprises said first material; and the entire area of said second bearing surface which area contacts the first bearing surface comprises said second material.

Said orthopaedic prosthetic joint may be selected from the group consisting of a hip joint, knee joint, spine joint, shoulder joint, elbow joint, tow joint, finger joint and ankle joint.

Said orthopaedic prosthetic joint is preferably a knee joint. The femoral component may comprise said first material; and the tibial component may comprise the second material.

According to a third aspect, there is provided a method of making an orthopaedic prosthetic joint as described in the first and/or second aspects, the method comprising a moulding (e.g. injection moulding) step and optional machining step to make the first joint component; and a moulding (e.g. injection moulding) step and optional machining step to make the second joint component.

According to a fourth aspect of the invention, there is provided the use of a first joint component as described according to the first and/or second aspects and a second joint component as described according to the first and/or second aspects in the manufacture of an orthopaedic prosthetic joint which comprises said first and second joint components bearing against one another for implantation into the human body, for example to replace a structural element of the body.

BRIEF DESCRIPTION OF THE DRAWINGS

For a better understanding of the invention, and to show how embodiments of the same may be carried into effect, reference will now be made, by way of example, to the accompanying diagrammatic drawings in which:

FIG. 1 shows the Volumetric Wear Rate in units of mm$^3$/MC.

BRIEF DESCRIPTION OF THE PREFERRED EMBODIMENTS AND BEST MODE

Any feature of any aspect of the invention or embodiment described herein may be combined with any other feature of any aspect of an invention or embodiment described herein *mutatis mutandis*.

Specific embodiments of the invention will now be described by way of example, with reference to FIG. 1 which is a graph showing volumetric wear rates for a series of samples.

The following materials are referred to hereinafter:

PEEK-OPTIMA (Trade Mark)—Long term implantable grade polyetheretherketone with a melt viscosity of approximately 0.45kNsm$^{-2}$, obtainable from Invibio Limited, UK;

GUR 1020 E (Trade Mark)—ultra-high molecular weight polyethylene containing Vitamin E obtained from Ticona;

GUR 1020 (Trade Mark)—as previous but not containing Vitamin E;

MOTIS (Trade Mark)—polyetheretherketone containing carbon fibres obtainable from Invibio Ltd, UK;

Barium sulphate—Barium sulphate grade 10175 from Merck.

Pin-on-disc testing was undertaken to assess various combinations of materials as described below.

EXAMPLES 1 to 8

Manufacture of Pins and Discs

Materials to be tested were machined into discs and pins as applicable. As manufactured, the pins had a diameter of 9 mm and length of 12 mm; the articulating end of the pins was machined flat. The discs were 10 mm thick, with the upper articulating surface of diameter 24.8 mm, with a circumferential groove to accommodate an o-ring to seal the chamber onto the disc. Prior to the start of the test, the discs and pins were soaked in deionized water for 56 days to allow for fluid uptake to reach equilibrium. The compositions of the discs and pins are detailed in Table 1.

TABLE 1

| Example No. | Composition | Test Specimen |
|---|---|---|
| 1. | PEEK-OPTIMA LT-1 with 6 wt % barium sulphate dispersed | Disc |
| 2. | PEEK-OPTIMA LT-1 with 6 wt % barium sulphate dispersed | Pin |
| 3. | GUR 1020 E | Pin |
| 4. | GUR 1020 E | Disc |
| 5. | PEEK OPTIMA LT-1 | Disc |
| 6. | MOTIS | Disc |
| 7. | GUR 1020 | Pin |
| 8. | PEEK-OPTIMA LT-1 | Pin |

EXAMPLE 9

Testing Equipment and Method

A T87 multi-station Pin-on-Disc machine (SuperPOD) was used, available from
Phoenix Tricology, UK. The discs were mounted in a test bath on top of a motion module. Water was circulated through the test bath at 37±3° C. A lubricant chamber (volume 15 ml) was mounted around each disc, so that each station had an independent volume of bovine serum lubricant. Each test pin was mounted on a carrier rod, restrained against rotation, with each pin independently loaded by means of a pneumatic piston. Air was supplied to the pistons from a common plenum chamber, resulting in constant air pressure applied to each piston, so each pin had an equal load applied. The load applied to each pin was 128 N, giving a nominal pressure of 2.01 MPa (pin diameter 9 mm).

The lubricant was Thermo Scientific Hyclone Wear Testing Fluid (Bovine serum) with 20 g/l total protein concentration. An antibiotic and fungicide were each added at a concentration of 1.5% to reduce the deterioration of the test fluid due to fungal and bacterial action during each 0.25 MC interval. At the end of each interval, the test fluid for each material combination was collected and frozen.

In the T87 SuperPOD, the pins were stationary and the discs followed an elliptical path without any rotation. The motion module was mounted on X and Y linear bearings and actuated through a double scotch yoke mechanism. The amplitude was 5 mm (stroke 10 mm) in the X direction and the amplitude was 2.5 mm (stroke 5 mm) in the Y direction. This gave a total path length of 24.2 mm per cycle. Throughout the test, the frequency of motion was 1 Hz. The motion of the SuperPOD meant the pins were subjected to full cross shear, but the discs were only subjected to cross shear in the limited zone in the middle of the "worn area" where the wear track crossed itself during the cycle.

For each combination of materials referred to, five specimens were tested in wear stations on the SuperPOD and one as a load soak control. The load soak was maintained under the same load as the wear specimens in an identical solution of bovine serum, but was not subjected to the sliding motion. The discs and pins were randomly assigned to the material pairing and either to a load soak or wear station. The location of the five stations testing each material pair was randomly distributed throughout the 100 stations on SuperPOD.

Every 0.25 MC the wear test was stopped for interval analysis and the test specimens removed for characterisation. At each interval, the lubricant was collected from each of the five wear stations for each material combination and frozen for potential future particle analysis. The pins and discs were cleaned and dried using the procedure described in ASTM F1714 "Standard Guide for Gravimetric Wear Assessment of Prosthetic Hip Designs in Simulator Devices". The o-rings, chambers and pin holders were subjected to the same cleaning process but were not dried. Photographs were taken of the pins and discs at each interval analysis.

The samples were weighed three times in rotation using a Sartorius balance (Bohemia, N.Y.). During each interval analysis, the load soak was dried and weighed and used to compensate for the fluid uptake of the specimens in the wear stations. The increase in mass of the load soak due to fluid uptake was added to the reduction in mass of each sample to give a corrected wear.

The gravimetric wear loss was converted to a volumetric wear loss using the material densities.

The wear factor was calculated for each material couple and was intended to allow comparisons between wear tests using different loads and sliding distance. The wear factor was derived from the Archard Wear Equation, which is based on the principle that the wear volume is proportional to the product of the sliding distance and real area of contact.

The wear factor k was calculated by:

$$k = \frac{V}{WxL}$$

where V is the volumetric wear ($mm^3/$), W is the normal load (N) and L the sliding distance (m).

The units are $mm^3/Nm$.

EXAMPLES 10-16

A series of wear couples were tested as detailed in Table 2 and volumetric wear rates established. Results are summarized in FIG. 1. For each wear couple the wear rate for the pin is shown on the left and that for the disc is shown on the right.

TABLE 2

| Example No. | Pin Material | Disc Material |
|---|---|---|
| 10. | 3 | 1 |
| 11. | 7 | 6 |
| 12. | 3 | 6 |
| 13. | 7 | 5 |
| 14. | 3 | 5 |
| 15. | 2 | 4 |
| 16. | 8 | 4 |

The following should be noted from FIG. 1.
(a) Example 13 relates to a combination of PEEK and ultra-light molecular weight polyethylene. The example can be compared to Example 11 which shows a combination of carbon fibre filled PEEK bearing against the same polyethylene. The comparison illustrates the effect on the wear of the polyethylene in adding filler into the PEEK-wear on the polyethylene increases significantly.
(b) Example 14 may be compared with Example 12 as described in (a) above and the same conclusions drawn.
(c) Example 10 includes a disc which comprises PEEK and barium sulphate bearing against a pin which comprises a polyethylene. This may be compared to Example 14 which is the same combination except that the disc comprises pure PEEK with no barium sulphate. In contrast to the effect of filler discussed in (a) and (b), it will be noted that the wear on the polyethylene for both Examples 10 and 14 are similar, meaning the addition of barium sulphate has had surprisingly little effect on wear.
(d) Example 15 includes a pin which comprises PEEK and barium sulphate bearing against a disc which comprises polyethylene. This may be compared to Example 16 which is the same combination except that the pin comprises pure PEEK with no barium sulphate. Thus, as described in (c), it should be appreciated that the comparison surprisingly shows addition of barium sulphate has little effect on wear.

This, it should be appreciated that barium sulphate can be added to PEEK for one part of a bearing component, at a level sufficient to give image contrast, with surprisingly little effect on wear of an associated polyethylene bearing component in use.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

What is claimed is:

1. An orthopaedic prosthetic joint comprising a joint couple comprising:
   (a) a first joint component having a first bearing surface comprising a first material which comprises a first polymer;
   (b) a second joint component having a second bearing surface comprising a second material which comprises a second polymer;
   wherein said first and second bearing surfaces are in sliding engagement with one another;
   wherein said first polymer is harder than said second polymer;
   wherein said first material includes a polyaryletherketone and barium sulfate
   wherein the joint is a knee joint;
   wherein the second material comprises polyethylene cross-linked by irradiation;
   wherein said first bearing surface includes at least 1 wt % barium sulphate and includes 30 wt % or less of barium sulphate,
   wherein said polyaryletherketone has a melt viscosity (MV) of at least $0.35$ $kNsm^{-2}$; and
   wherein said first joint component consists essentially of polyetheretherketone and barium sulphate; and at leas 80 wt % of said second joint component is made up of said second polymer.

2. An orthopaedic prosthetic joint comprising a joint couple comprising:
   (a) a first joint component having a first bearing surface made of a first polymer; and
   (b) a second joint component having a second bearing surface made of a second polymer;
   wherein said first and second bearing surfaces are in sliding engagement with one another;
   wherein said first bearing surface is made of a first material which is harder than a second material from which the second joint surface is made;
   wherein said first material comprise a polyaryletherketone and barium sulphate;
   wherein the joint is a knee joint;
   wherein the second material comprises polyethylene cross-linked by irradiation; and
   wherein said first bearing surface includes at least 1 wt % barium sulphate and includes 30 wt % or less of barium sulphate;
   wherein said polyaryletherketone has a melt viscosity (MV) of at least $kNsm^2$, and wherein said first joint component consists essentially of polyetheretherketone and barium sulphate; and at least 80 wt % of said second joint component is made up of said second polymer.

3. A joint according to claim 1, wherein said barium sulphate has a $D_{10}$ particle size in the range 0.1 to 1.0 μm.

4. A joint according to claim 1, wherein the ratio of the wt % of barium sulphate to the wt % of said first polymer is greater than 0.04 and is less than 0.4.

5. A joint according to claim 1, wherein said polyaryletherketone has a repeat unit of formula (I)

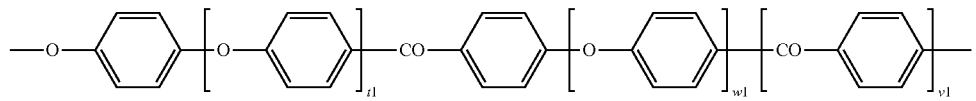

where t1 and w1 independently represent 0 or 1 and v1 represents 0, 1 or 2.

6. A joint according to claim 1, wherein said polyaryletherketone has a crystallinity of greater than 25%.

7. A joint according to claim 1, wherein said second material comprises at least 60 wt % of a polymeric material selected from polyethylene, a polyurethane and a polyamide.

8. A joint according to claim 2, wherein said barium sulphate has a $D_{10}$ particle size in the range 0.1 to 1.0 μm.

9. A joint according to claim 2, wherein the ratio of the wt % of barium sulphate to the wt % of said first polymer is greater than 0.04 and is less than 0.4.

10. A joint according to claim 2, wherein said polyaryletherketone has a repeat unit of formula (I)

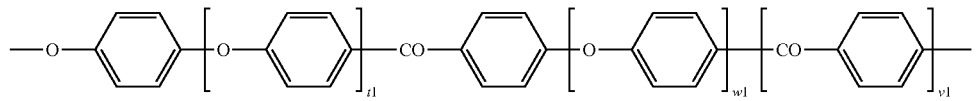

where t1 and w1 independently represent 0 or 1 and v1 represents 0, 1 or 2.

11. A joint according to claim 2, wherein said polyaryletherketone has a crystallinity of greater than 25%.

* * * * *

UNITED STATES PATENT AND TRADEMARK OFFICE
CERTIFICATE OF CORRECTION

PATENT NO. : 11,103,352 B2
APPLICATION NO. : 16/538130
DATED : August 31, 2021
INVENTOR(S) : Adam Briscoe Page 1 of 1

It is certified that error appears in the above-identified patent and that said Letters Patent is hereby corrected as shown below:

On the Title Page

Related U.S. Application Data should read:
(63) Continuation of U.S. Application No. 14/438,672, filed on April 27, 2015, which is a National Stage Entry application of International Application No. PCT/GB2013/052770 filed on October 24, 2013, now abandoned.

(30) Foreign Application Priority Data should read:
Nov. 1, 2012 (GB) ............................ 1219686.1

In the Claims

In Claim 1, Column 9, Line 21, change "sulfate" to –sulphate–

In Claim 1, Column 9, Line 31, change "leas" to –least–

Signed and Sealed this
Second Day of November, 2021

Drew Hirshfeld
*Performing the Functions and Duties of the
Under Secretary of Commerce for Intellectual Property and
Director of the United States Patent and Trademark Office*